(12) United States Patent
Pietrini et al.

(10) Patent No.: US 10,981,710 B1
(45) Date of Patent: Apr. 20, 2021

(54) TAKE-BACK LINER AND TAKE-BACK KIT THEREFROM

(71) Applicant: American RX Group, LLC, Eden Prairie, MN (US)

(72) Inventors: Michael J. Pietrini, Maple Grove, MN (US); Craig A. Whaley, Otsego, MN (US); Matthew A. Machesky, Saint Cloud, MN (US)

(73) Assignee: American RX Group, LLC, Eden Prairie, MN (US)

( * ) Notice: Subject to any disclaimer, the term of this patent is extended or adjusted under 35 U.S.C. 154(b) by 34 days.

(21) Appl. No.: 16/556,949

(22) Filed: Aug. 30, 2019

(51) Int. Cl.
  *B65D 77/06* (2006.01)
  *B65D 5/02* (2006.01)

(52) U.S. Cl.
  CPC ......... *B65D 77/062* (2013.01); *B65D 5/0236* (2013.01)

(58) Field of Classification Search
  CPC .... B65D 77/062; B65D 5/0236; B65D 5/605; B31B 2120/408; B31B 2120/40; B31B 50/624
  USPC ............ 229/117.27, 117.32, 117.33; 493/98; 156/265
  See application file for complete search history.

(56) References Cited

U.S. PATENT DOCUMENTS

| | | | |
|---|---|---|---|
| 1,517,964 A * | 12/1924 | Drysdale | B65D 5/606 229/164.2 |
| 2,114,623 A | 4/1938 | Bergstein | |
| 2,364,012 A | 11/1944 | Walton et al. | |
| 2,388,190 A * | 10/1945 | Smart | B65D 5/3621 229/117 |
| 3,113,712 A | 12/1963 | Kindseth | |
| 3,181,583 A | 5/1965 | Lingenfelter | |
| 3,182,883 A * | 5/1965 | Doble, Jr. | B65D 5/606 229/117.27 |
| 3,456,861 A | 7/1969 | Wettlen | |
| 3,576,290 A | 4/1971 | Marchisen | |
| 4,492,295 A | 1/1985 | DeWoolfson | |
| 4,572,377 A | 2/1986 | Beckett | |
| 4,824,261 A | 4/1989 | Provost | |
| 4,872,588 A | 10/1989 | Texidor | |

(Continued)

FOREIGN PATENT DOCUMENTS

| | | |
|---|---|---|
| EP | 1964786 A1 | 9/2008 |
| EP | 2110095 A1 | 10/2009 |

*Primary Examiner* — Christopher R Demeree
(74) *Attorney, Agent, or Firm* — Albert W. Watkins

(57) ABSTRACT

A box and take-back bag liner suitable for transporting regulated and controlled medications to a disposal site are together shipped in a first configuration as a substantially flat, compact, and durable take-back kit. The take-back kit is readily assembled to a second configuration defining a bag-lined receptacle. When the receptacle requires replacement, such as when full or otherwise determined, the box and bag liner are reconfigured to a third configuration that transports the contents of the bag liner to the disposal facility. The box incorporates a double-sealed vertical side seam, an auto-folding bottom having a pair of mutually engaging notches and slits, a multi-layer top, and pre-affixed tapes and glues. The liner incorporates both a rib and groove seal and a tape seal to provide a liquid tight and tamper evident seal. The combined box and liner provide structural integrity, security, tamper resistance and evidence, and governmental regulation compliance.

9 Claims, 4 Drawing Sheets

(56) References Cited

U.S. PATENT DOCUMENTS

| | | |
|---|---|---|
| 4,907,717 A | 3/1990 | Kubofcik |
| 4,969,596 A | 11/1990 | Schulbaum |
| 5,048,692 A | 9/1991 | Handler et al. |
| 5,156,294 A | 10/1992 | Nichols |
| 5,163,555 A | 11/1992 | West et al. |
| 5,186,900 A | 2/1993 | Jensen et al. |
| 5,339,959 A | 8/1994 | Cornwell |
| 5,407,277 A | 4/1995 | Burke et al. |
| 5,456,928 A | 10/1995 | Hustad et al. |
| 5,560,512 A | 10/1996 | Hahn |
| 5,842,916 A | 12/1998 | Gerrity |
| 5,851,071 A | 12/1998 | Arnell |
| 6,003,666 A | 12/1999 | Dougherty |
| 6,012,844 A | 1/2000 | Huseman et al. |
| 6,062,001 A | 5/2000 | Kunik |
| 6,149,302 A | 11/2000 | Taheri |
| 6,416,221 B2 | 7/2002 | Price |
| 6,431,752 B1 | 8/2002 | Diplock |
| 7,254,873 B2 | 8/2007 | Stolmeier et al. |
| 7,798,711 B2 | 9/2010 | Plunkett et al. |
| 7,841,511 B2 * | 11/2010 | Fogle .................. B65D 5/10 229/117 |
| 8,163,045 B2 | 4/2012 | Kunik et al. |
| 8,195,511 B2 | 6/2012 | Bowles et al. |
| 8,268,073 B2 | 9/2012 | Kunik et al. |
| 10,150,613 B2 | 12/2018 | Kunik et al. |
| 2003/0222132 A1 | 12/2003 | Esakov et al. |
| 2005/0046567 A1 | 3/2005 | Mortenson et al. |
| 2005/0065640 A1 | 3/2005 | Mallett et al. |
| 2005/0216120 A1 | 9/2005 | Rosenberg et al. |
| 2007/0098305 A1 | 5/2007 | Tilman |
| 2007/0278140 A1 | 12/2007 | Mallett et al. |
| 2008/0044110 A1 | 2/2008 | Garger |
| 2008/0056622 A1 | 3/2008 | Austreng et al. |
| 2009/0043253 A1 | 2/2009 | Podaima |
| 2009/0271316 A1 | 10/2009 | Kranyec |
| 2010/0051152 A1 | 3/2010 | McElaney et al. |
| 2011/0004761 A1 | 1/2011 | Thackray et al. |
| 2011/0209392 A1 | 9/2011 | Kunik et al. |
| 2012/0260566 A1 | 10/2012 | Kunik et al. |
| 2013/0061788 A1 | 3/2013 | Kunik et al. |
| 2013/0097920 A1 | 4/2013 | Kunik et al. |
| 2015/0152348 A1 | 6/2015 | Tusa et al. |
| 2019/0337668 A1 * | 11/2019 | Block .................. B65D 5/3635 |

* cited by examiner

TAKE-BACK LINER AND TAKE-BACK KIT THEREFROM

BACKGROUND OF THE INVENTION

1. Field of the Invention

The present invention pertains generally to the field of medication disposal, including hazardous and prescription medications. More particularly, the present invention pertains to an easy to assemble and use box, and a tamper-evident liner that together facilitate convenient disposal and durable packaging that is compliant with governmental regulations for the transport of such medications to an appropriate disposal facility through a common carrier.

2. Description of the Related Art

Medicine has always played a vital role in the life of humans. An appropriate treatment can literally make the difference between life and death. Early medicine relied heavily on plant and botanical based medications in the treatment of ailments. While a few of these medications could be hazardous or addictive if misused, the vast majority were relatively weak and non-addictive.

However, and in great contrast to early medications, for much of the past hundred years there has been a revolution in the formulation of medications. This has included both the identification and concentration of medicinal plants and botanicals, and the development and synthesis of medications that might not otherwise be available in nature. As a result, there has been an increased risk of accidental or intentional misuse of medications by persons other than the patient that can lead to great harm. In consideration thereof, many of these medications are only available by prescription, and a further subset are even more tightly controlled and regulated.

For some time, the only convenient way for an individual to permanently dispose of medications was disposal into household sewage and septic systems. Unfortunately, as the effectiveness of the medications has improved, so has the quantity of medication being released into ground and surface water. The amount of medication being disposed has risen to the point where both wildlife and even humans consuming treated water down stream are being exposed to undesirably high levels of medications. For exemplary and non-limiting example, some cancer medication molecules are too small to be filtered out even with very advanced and expensive municipal water filtration systems.

In consideration thereof, many years ago a system was implemented whereby a person could send their medications through the mail to an appropriate disposal site. Typically the disposal site would be a commercial incinerator facility, where the medications received would be destroyed through combustion, leaving only harmless ash as a residue. Since the US mail is quite secure, beginning with a mail box designed to resist tampering and through the mail handling enforcement of strict laws and strong penalties, such medications were expected to be delivered and disposed of in an efficient manner.

However, there were several deficiencies with this mail-back approach. One drawback is that a person would be required to first package and then pay postage to dispose of their medications, when they could instead simply flush them down the toilet or throw them in the trash for no additional cost and very minimal effort. A second drawback was inconsistent packaging by individuals, some packages which could fail during ordinary handling and transport. Another drawback was that there was no way to determine if a postal employee tampered with the mailed prescriptions. In some instances, such as when a stock prescription drug expires due to age on the shelf of a pharmacy, a substantial amount of a drug may require disposal. This expired prescription drug might be worth substantial money on the street, and might also be targeted by drug abusers or drug seekers. With ordinary postal packaging, there is no effective way to determine if the package has been tampered with prior to reaching the disposal facility. In addition, HIPPA compliance can be an issue with handling of the medications being mailed back, since patient identification is on the exterior envelope, and patient information and medication are listed on the medication containers.

A further improvement was the provision of kiosks and receptacles to law enforcement agencies. Pharmaceuticals and other substances can be dropped at the agency, where the substances are collected for ultimate shipment to a disposal facility. While this eliminates the need for postage, the law enforcement agencies are burdened with the monitoring and access control. As may be easily appreciated, most law enforcement agencies already are overloaded with normal duties, and this collection function only increases the overall workload. Furthermore, this approach still fails to provide an effective way to determine if a package containing controlled substances has been tampered with prior to reaching the disposal facility. In addition, some of the medications can be quite hazardous if law enforcement personnel are accidentally exposed, creating an undesirable additional workplace hazard.

Recognizing the need for improved handing and disposal of medications, the US Government set forth new requirements. These new requirements have altered and improved the methods and apparatus used in the handing and disposal of medications.

An approach that has been adopted responsive to those new regulations is the provision of a secure kiosk, typically resembling a mailbox and incorporating many features similar thereto. Exemplary U.S. patents and published applications, the teachings which are incorporated herein by reference, include: U.S. Pat. No. 4,492,295 by DeWoolfson, entitled "Automated redemption center for metal containers"; U.S. Pat. No. 5,560,512 by Hahn, entitled "Anti-scavenging device for use with receptacles"; U.S. Pat. No. 5,842,916 by Gerrity, entitled "Method and apparatus for conditioning coins prior to discrimination"; U.S. Pat. No. 8,195,511 by Bowles et al, entitled "Secondary market and vending system for devices"; 2003/0222132 by Esakov et al, entitled "Mail collection bag"; 2005/0046567 by Mortenson et al, entitled "Method and system for utilizing multiple sensors for monitoring container security, contents and condition"; 2005/0065640 by Mallett et al, entitled "Methods of sorting waste"; 2005/0216120 by Rosenberg et al, entitled "Automatic vending machine and method"; 2007/0278140 by Mallett et al, entitled "Restricted access waste sorting system"; 2009/0271316 by Kranyec, entitled "Mailing kiosk with safeguards and methods of use"; 2012/0004761 by Madruga, entitled "Depository unit with user interaction"; and 2015/0152348 by Tusa et al, entitled "Systems and methods for collecting, transporting and repurposing or destroying unused pharmaceuticals".

A person may bring and drop their unused medications into a convenient kiosk. The medications in the kiosk are then collected periodically, and securely transported to a disposal site. However, and as evident from the aforementioned patents and published applications, the apparatus and method of periodic collection varies greatly among the different kiosk designs.

Some kiosks have simple tubs at the bottom of the kiosk, again very closely resembling a standard mailbox. Unfortunately, this approach provides no security or evidence of tampering with the collected medications. In order to provide such security and tamper indication, the medications must be further handled, which creates a loss of control and an opportunity for subterfuge. In addition, handling of the medications by an intermediate recipient is both a violation of DEA guidelines, and will lead to HIPPA violations, once again because the patient information and type of medication are each listed on prescription containers.

A few of the aforementioned artisans, and a number of others, have considered transporting hazardous materials in a "bag-in-a-box". Exemplary "bag-in-a-box" U.S. patents and published applications, the teachings which are incorporated herein by reference, include: U.S. Pat. No. 4,907,717 by Kubofcik, entitled "Low-level radiation waste management system"; U.S. Pat. No. 4,969,596 by Schulbaum, entitled "Infectious waste disposal container"; U.S. Pat. No. 5,163,555 by West et al, entitled "Hazardous waste disposal container"; U.S. Pat. No. 6,003,666 by Dougherty, entitled "Method and apparatus for storing and shipping hazardous materials"; U.S. Pat. No. 8,268,073 by Kunik et al, entitled "System and method for making cement and cement derived therefrom"; U.S. Pat. No. 10,150,613 by Kunik et al, entitled "Packaging designed to be a fuel component and methods for making and using same"; 2013/0061788 by Kunik et al, entitled "System and method for making cement and cement derived therefrom"; and 2013/0097920 by Kunik et al, entitled "System and method for making cement and cement derived therefrom".

There are a number of benefits inherent in the "bag-in-a-box" approach. With a liner bag, individual prescriptions do not require handling. Further, when properly arranged, a person will not even have the opportunity to see into the bag, and can initiate closing of the bag while the bag and box are even still inside of the kiosk. In such instances, there is no "accidental" opportunity for HIPPA violations. In addition, when materials are appropriately selected, both the bag and box will combust. Since ordinary cardboard combusts well, well-known cardboard box-making techniques may readily be used. Similarly, most plastics are readily combustible, particularly in an incinerator. Furthermore, a properly designed box serves as a protective shipping container, protecting the bag against rips, punctures, tears, and other failure modes, allowing the contents to be transported using either private (commercial) couriers or governmental couriers such as the US Post Office. A properly designed "bag-in-a-box" will contain any liquids within the bag, thereby protecting both the box and other adjacent packages from undesirable liquid exposure.

Noteworthy here is that if a medication container drops outside of the liner bag in the interior of the kiosk, and presuming the persons managing the kiosk respond according to the letter of the law, this displaced medication container will trigger a hazmat event requiring a special hazmat team to come to the site and move the displaced medication container into the liner bag. Similarly, if the liner bag leaks either liquids or spills any contents, this too requires the intervention of the hazmat team. As may be appreciated, triggering the need for hazmat intervention is both very time consuming and very expensive. Further, the presence of the hazmat team can be very disruptive and harmful to a business such as retail pharmacy, since customers will likely divert from entering the pharmacy and may mistakenly assume that the business is not operating in a safe manner.

While this "bag-in-a-box" approach has offered much advantage over the previous methods and apparatus, there is still undesirable opportunity for failure. Since each failure is procedurally required to trigger a hazmat intervention, even if the failure rate is quite small such failures will multiply the actual cost of each "bag-in-a-box".

One common cause for box failure in the prior art is generically referred to as user error. Failure to properly assemble a box can lead to failure. As one non-limiting example, a member that provides necessary structural benefit might be incorrectly folded or placed, meaning the final package does not have the required structural integrity. As another non-limiting example, a person might improperly apply packaging tape, or the tape itself might be old or otherwise inadequate for the application. Unfortunately, the prior art "bag-in-a-box" constructions are very susceptible to these and other types of user error.

A number of other artisans have designed containers for more diverse application of the "bag-in-a-box" approach. Exemplary U.S. and Foreign patents and published applications, the teachings which are incorporated herein by reference, include: U.S. Pat. No. 2,114,623 by Bergstein, entitled "Method of providing for internal atmospheric expansion of filled bags and hermetically sealing same"; U.S. Pat. No. 2,364,012 by Walton et al, entitled "Container"; U.S. Pat. No. 3,113,712 by Kindseth, entitled "Transporting and dispensing container"; U.S. Pat. No. 3,456,861 by Wettlen, entitled "Package comprising a thin bag and a double-folded stiffening inserted into the body of the bag, and the procedure for the production of this package"; U.S. Pat. No. 3,576,290 by Marchisen, entitled "Bag in a box for frozen eggs or the like"; U.S. Pat. No. 4,872,588 by Texidor, entitled "Lined carton"; U.S. Pat. No. 5,156,294 by Nichols, entitled "Foldable box with internal bag"; U.S. Pat. No. 6,416,221 by Price, entitled "Thermoplastic bag with offset fastener"; and U.S. Pat. No. 7,798,711 by Plunkett et al, entitled "Flexible liner for FIBC or bag-in-box container systems".

In spite of the number of "bag-in-a-box" configurations outlined in these aforementioned patents, a durable, easy to assemble, and easy to use box and bag that is suitable for flat package shipment to a kiosk location prior to use, and that is also suitable for securely and safely transporting prescriptions and other medications that have been inserted into the box and bag to a disposal facility through a common carrier has remained an unsatisfied objective.

While the relevance of the following patents and published applications is not evident from either the field of the present invention or the many documents incorporated herein, the relevance will become apparent upon a review and understanding of the present disclosure, and so these documents are presented and incorporated by reference herein below.

A number of bags with reclosable fasteners and an adhesive flap are known. Exemplary U.S. and Foreign patents and published applications, the teachings which are incorporated herein by reference, include: U.S. Pat. No. 5,048,692 by Handler et al, entitled "Bag closure structure in which a single resealable closure acts as both the primary and secondary closures"; U.S. Pat. No. 5,456,928 by Hustad et al, entitled "Tamper-evident, flexible, reclosable package"; U.S. Pat. No. 6,149,302 by Taheri, entitled "Plastic bag with tamper-evident closure"; U.S. Pat. No. 7,254,873 by Stolmeier et al, entitled "Scored tamper evident fastener tape"; 2007/0098305 by Tilman, entitled "Slider end stop for a reclosable bag and methods"; 2008/0044110 and WO 2006/037240 by Garger, entitled "Paper or plastic bag"; 2008/0056622 by Austreng et al, entitled "Resealable package with tamper-evident structure and method for making same"; 2010/0051152 by McElaney et al, entitled "Disposable protector for electronic devices"; EP 1,964,786 by Doue, entitled "Bag adapted for manual filling and sealing"; and EP 2,110,095 by Duerrbeck et al, entitled "Bag, in particular for taking up contaminated objects".

While some of these bags are provided with a tamper-evident closure, such closures are normally formed or affixed at the factory using specialized equipment. As a result, such closures are of little value in the closing of a bag that has been filled within a kiosk and which must then be closed manually by a person.

Other artisans have disclosed various techniques for forming tamper-evident bag closures. Exemplary U.S. and Foreign patents and published applications, the teachings which are incorporated herein by reference, include: U.S. Pat. No. 4,572,377 by Beckett, entitled "Packaging structure"; U.S. Pat. No. 4,824,261 by Provost, entitled "Reclosable bag and hook and loop sealing strips for use therein"; U.S. Pat. No. 5,407,277 by Burke et al, entitled "Tamper evident bag with auxiliary bag"; U.S. Pat. No. 5,851,071 by Arnell, entitled "Plastic bag with permanent sealing zipper"; and U.S. Pat. No. 6,431,752 by Diplock, entitled "Plastic coin transport bag".

An additional noteworthy patent, the relevant teachings and contents which are incorporated herein by reference, is U.S. Pat. No. 5,339,959 by Cornwell, entitled "Disposable medical waste bag". This patent describes a twist seal folded and taped to secure, but without a box, used for medical waste. In addition, this patent discusses the benefit of fabricating such a bag from polyethylene for ultimate incineration.

Additional U.S. and Foreign patents and published applications of varying relevance, the relevant teachings and contents which are incorporated herein by reference, include: U.S. Pat. No. 3,181,583 by Lingenfelter, entitled "Reclosable plastic container"; U.S. Pat. No. 6,012,844 by Huseman et al, entitled "Selectively closeable plastic film bag"; U.S. Pat. No. 6,062,001 by Kunik, entitled "Sharps disposal container"; U.S. Pat. No. 8,163,045 by Kunik et al, entitled "Method and system of making a burnable fuel"; 2009/0043253 by Podaima, entitled "Smart medical compliance method and system"; 2011/0209392 and WO 2011/105990 by Kunik et al, entitled "Coated particulate and shaped fuels and methods for making and using same"; and 2012/0260566 by Kunik et al, entitled "Systems of making a burnable fuel".

In addition to the foregoing patents, Webster's New Universal Unabridged Dictionary, Second Edition copyright 1983, is incorporated herein by reference in entirety for the definitions of words and terms used herein.

As may be apparent, in spite of the enormous advancements and substantial research and development that has been conducted, there still remains a need for an improved secure and governmentally compliant "bag-in-a-box" construction for the transport of prescription medications. Since many of these prescriptions are controlled substances, this creates additional expectation and requirement for the "bag-in-a-box". As noted herein above, tamper evident construction is critical to the secure handling of controlled substances. Further, in order to be widely adopted, the assembly and use of the "bag-in-a-box" must be intuitive and quick. While tape seals created with the well-known packaging tape guns would at first blush appear to be suitable for the present application, the opposite is true. The sharp, typically serrated cutter edge on the tape dispenser creates the undesirable potential for the person tasked with sealing conventional liner systems at risk of being cut. A cut from the tape dispenser breaks the person's own skin barrier, making them very susceptible, which can leave them even more susceptible to exposure to damaged or otherwise leaking medication containers. As noted above, some of these medications are extremely potent. Furthermore, both the packaging tape and the application of the tape will vary from one person and package to another, meaning the durability of the "closed and sealed" bag-in-a-box is unpredictable. Once again, even a seemingly minor leak requires the initiation of an entire hazmat event.

As may be appreciated from the foregoing, a durable, easily assembled, and easily used box and bag suitable for securely and safely transporting prescriptions and other medications remains an unsatisfied objective.

SUMMARY OF THE INVENTION

In a first manifestation, the invention is, in combination, a box and a bag liner retained within the box. The combination box and bag liner have a first substantially void free flat receptacle configuration for storage and shipping of box and liner kits, a second receptacle configuration into which articles may be inserted, and a third transport configuration enclosing said articles within each of said box and said bag liner. The box comprises a blank fabricated from a unitary planar sheet having a plurality of fold lines. The fold lines define first, second, third, and fourth vertical side walls hinged to adjacent ones of the side walls. First and second bottom side flaps are hinged to first and third vertical side walls, respectively. A first bottom main flap is hinged to the second vertical side wall, and has at least one crease line formed therein dividing the first bottom main flap into first and second portions and further has at least one notch terminating with a slit. The slit is formed in the second portion of the first bottom main flap. A second bottom main flap is hinged to the fourth vertical side wall, and has at least one crease line formed therein dividing the second bottom main flap into first and second portions and further has at least one notch terminating with a slit. The slit is formed in the second portion of the second bottom main flap. An inside top lid is hinged to a one of the first, second, third, and fourth vertical side walls. An outside top lid is hinged to a first one of the first, second, third, and fourth vertical side walls. First, second, and third outside top lid side flaps are each hinged to the outside top lid. A first tape strip affixes the first bottom side flap to the first bottom main flap on a first side of the first bottom main flap crease line. A second tape strip affixes the second bottom side flap to the second bottom main flap on a first side of the second bottom main flap crease line. A third tape strip is affixed to a one of the said second bottom side flap and first bottom main flap and is disconnected from another of the second bottom side flap and first bottom main flap when the combination box and bag liner is in the first substantially void free flat receptacle configuration. The third tape strip is further configured to affix the second bottom side flap to the first bottom main flap on a second side of the first bottom main flap crease line when the combination box and bag liner is in the second receptacle configuration into which articles may be inserted and is also configured to affix the second bottom side flap to the first bottom main flap on a second side of the first bottom main flap crease line when the combination box and bag liner is in the third transport configuration. A fourth tape strip is affixed to a one of the first bottom side flap and second bottom main flap and is disconnected from another of the first bottom side flap and second bottom main flap when the combination box and bag liner is in the first substantially void free flat receptacle configuration. The fourth tape strip is further configured to affix the first bottom side flap to the second bottom main flap on a second side of the second bottom main flap crease line when the combination box and bag liner is in the second receptacle configuration into which articles may be inserted and configured to affix the second bottom side flap to the first bottom main flap on a second side of the first bottom main flap crease line when the combination box and bag liner is in said third transport configuration. The first bottom main flap slit is disconnected from the second bottom main flap slit when the combination box and bag liner is in the first substantially void free flat receptacle configuration and is coupled with the second bottom main flap slit when the combination box and bag liner is in the second receptacle configuration and when the combination box and bag liner is in the third transport configuration. A fifth tape strip is affixed to a one of the first, second, third, and fourth vertical side walls and the outside top lid, and is disconnected from each other of the first, second, third, and fourth vertical side walls and the outside top lid when the combination box and bag liner is in the first substantially void free flat receptacle configuration and when the combination box and bag liner is in the second receptacle configuration. The fifth tape strip is configured to affix a second one of the first, second, third, and fourth vertical side walls to the outside top lid when the combination box and bag liner is in the third transport configuration. A sixth tape strip is affixed to a one of the first, second, third, and fourth vertical side walls and the outside top lid and is disconnected from each other of the first, second, third, and fourth vertical side walls and the outside top lid when the combination box and bag liner is in the first substantially void free flat receptacle configuration and when the combination box and bag liner is in the second receptacle configuration. The sixth tape strip is configured to affix a third one of the first, second, third, and fourth vertical side walls to the outside top lid when the combination box and bag liner is in the third transport configuration. A seventh tape strip is affixed to a one of the first, second, third, and fourth vertical side walls and the outside top lid and is disconnected from each other of the first, second, third, and fourth vertical side walls and the outside top lid when the combination box and bag liner is in the first substantially void free flat receptacle configuration and when the combination box and bag liner is in the second receptacle configuration. The seventh tape strip is configured to affix a fourth one of the first, second, third, and fourth vertical side walls to the outside top lid when the combination box and bag liner is in the third transport configuration. The bag liner comprises a pair of opposed side walls affixed to each other to define an open-top bag. A liner zip is configured to selectively close the open-top bag. A liner tape is displaced farther from the open-top than the liner zip, and is configured to secure a twice-folded liner zip against a one of said pair of opposed side walls.

In a second manifestation, the invention is box having a first substantially void free flat receptacle configuration, a second receptacle configuration into which articles may be inserted, and a third transport configuration enclosing the articles within the box. The box comprises a blank fabricated from a unitary planar sheet having a plurality of fold lines. The fold lines define first, second, third, and fourth vertical side walls hinged to adjacent ones of the side walls. First and second bottom side flaps are hinged to first and third vertical side walls, respectively. A first bottom main flap is hinged to the second vertical side wall, and has at least one crease line formed therein dividing the first bottom main flap into first and second portions and further has at least one notch terminating with a slit. The slit is formed in the second portion of the first bottom main flap. A second bottom main flap is hinged to the fourth vertical side wall, and has at least one crease line formed therein dividing the second bottom main flap into first and second portions and further has at least one notch terminating with a slit. The slit is formed in the second portion of the second bottom main flap. An inside top lid is hinged to a one of the first, second, third, and fourth vertical side walls. An outside top lid is hinged to a first one of the first, second, third, and fourth vertical side walls. First, second, and third outside top lid side flaps are each hinged to the outside top lid. A first tape strip affixes the first bottom side flap to the first bottom main flap on a first side of the first bottom main flap crease line. A second tape strip affixes the second bottom side flap to the second bottom main flap on a first side of the second bottom main flap crease line. A third tape strip is affixed to a one of the said second bottom side flap and first bottom main flap and is disconnected from another of the second bottom side flap and first bottom main flap when the box is in the first substantially void free flat receptacle configuration. The third tape strip is further configured to affix the second bottom side flap to the first bottom main flap on a second side of the first bottom main flap crease line when the box is in the second receptacle configuration into which articles may be inserted and is also configured to affix the second bottom side flap to the first bottom main flap on a second side of the first bottom main flap crease line when the box is in the third transport configuration. A fourth tape strip is affixed to a one of the first bottom side flap and second bottom main flap and is disconnected from another of the first bottom side flap and second bottom main flap when the box is in the first substantially void free flat receptacle configuration. The fourth tape strip is further configured to affix the first bottom side flap to the second bottom main flap on a second side of the second bottom main flap crease line when the box is in the second receptacle configuration into which articles may be inserted and configured to affix the second bottom side flap to the first bottom main flap on a second side of the first bottom main flap crease line when the box is in said third transport configuration. The first bottom main flap slit is disconnected from the second bottom main flap slit when the box is in the first substantially void free flat receptacle configuration and is coupled with the second bottom main flap slit when the box is in the second receptacle configuration and when the box is in the third transport configuration. A fifth tape strip is affixed to a one of the first, second, third, and fourth vertical side walls and the outside top lid, and is disconnected from each other of the first, second, third, and fourth vertical side walls and the outside top lid when the box is in the first substantially void free flat receptacle configuration and when the box is in the second receptacle configuration. The fifth tape strip is configured to affix a second one of the first, second, third, and fourth vertical side walls to the outside top lid when the box is in the third transport configuration.

A sixth tape strip is affixed to a one of the first, second, third, and fourth vertical side walls and the outside top lid and is disconnected from each other of the first, second, third, and fourth vertical side walls and the outside top lid when the box is in the first substantially void free flat receptacle configuration and when the box is in the second receptacle configuration. The sixth tape strip is configured to affix a third one of the first, second, third, and fourth vertical side walls to the outside top lid when the box is in the third transport configuration. A seventh tape strip is affixed to a one of the first, second, third, and fourth vertical side walls and the outside top lid and is disconnected from each other of the first, second, third, and fourth vertical side walls and the outside top lid when the box is in the first substantially void free flat receptacle configuration and when the box is in the second receptacle configuration. The seventh tape strip is configured to affix a fourth one of the first, second, third, and fourth vertical side walls to the outside top lid when the box is in the third transport configuration.

In a third manifestation, the invention is a bag liner. The liner comprises a pair of opposed side walls affixed to each other to define an open-top bag. A liner zip is configured to selectively close the open-top bag. A liner tape is displaced farther from the open-top than the liner zip, and is configured to secure a twice-folded liner zip against a one of the pair of opposed side walls.

OBJECTS OF THE INVENTION

Exemplary embodiments of the present invention solve inadequacies of the prior art by providing a box and take-back bag liner suitable for transporting highly regulated and controlled medications to a disposal site. The box and liner are shipped in a first configuration as a substantially flat and compact take-back kit with few voids. The take-back kit is readily assembled to a second configuration defining a receptacle. When the receptacle is to be replaced, such as when full or otherwise scheduled or determined, the box and bag liner are reconfigured to a third configuration that transports the contents of the bag liner to a disposal or other facility. The box incorporates a double-sealed vertical side seam, an auto-folding bottom, and a multi-layer top, with all box edges reinforced by adjacent box material. Pre-placed adhesives work with the box construction to provide predictable and compliant structural integrity. The liner incorporates a rib and groove seal and a tape seal to provide a substantially liquid tight and tamper evident seal.

The present invention and the preferred and alternative embodiments have been developed with a number of objectives in mind. While not all of these objectives are found in every embodiment, these objectives nevertheless provide a sense of the general intent and the many possible benefits that are available from embodiments of the present invention.

A first object of the invention is to provide an improved governmentally compliant "bag-in-a-box" construction for the transport of prescription medications through a common carrier. A second object of the invention is to provide a tamper-evident and generally leak-proof seal when the bag liner is closed for transport of prescription medications, for accountability and secure handling of controlled substances. Another object of the present invention is to provide a durable box that may be folded compactly, such as relatively flat, for storage and shipping to a collection location, and which is intuitive, quick, and easy to assemble when needed at the collection location. As a corollary thereto, a further object of the present invention is to provide all means of affixing and securing already affixed to the box in a ready-to-activate arrangement. As an additional corollary thereto, an additional object of the invention is to provide a design that reduces the chance of user error. As a further corollary thereto, yet another object of the invention is to provide a box that will expand from a flat configuration by a simple pull, and during the expansion will simultaneously form and define the box bottom. A further object of the invention is to provide a lightweight, predictably structurally strong, and low cost container that is relatively easy to manufacture and suitable for securely and safely transporting prescriptions and other medications. Yet another object of the present invention is to incorporate materials into the bag liner and box that may be incinerated with any articles collected therein.

BRIEF DESCRIPTION OF THE DRAWINGS

The foregoing and other objects, advantages, and novel features of the present invention can be understood and appreciated by reference to the following detailed description of the invention, taken in conjunction with the accompanying drawings, in which.

DESCRIPTION OF THE PREFERRED EMBODIMENT

Manifested in the preferred embodiment, the present invention provides a box 10 and take-back bag liner 40 that together may be shipped in a first configuration as a substantially flat and compact take-back kit with few voids. The take-back kit is readily assembled from the flat first configuration into a second receptacle configuration, as will be described herein below. When the receptacle is to be replaced, such as when full or otherwise scheduled or determined, the box 10 and bag liner 40 are reconfigured to a third transport configuration used to transport the contents of bag liner 40 to a disposal or other facility.

Figure 1:
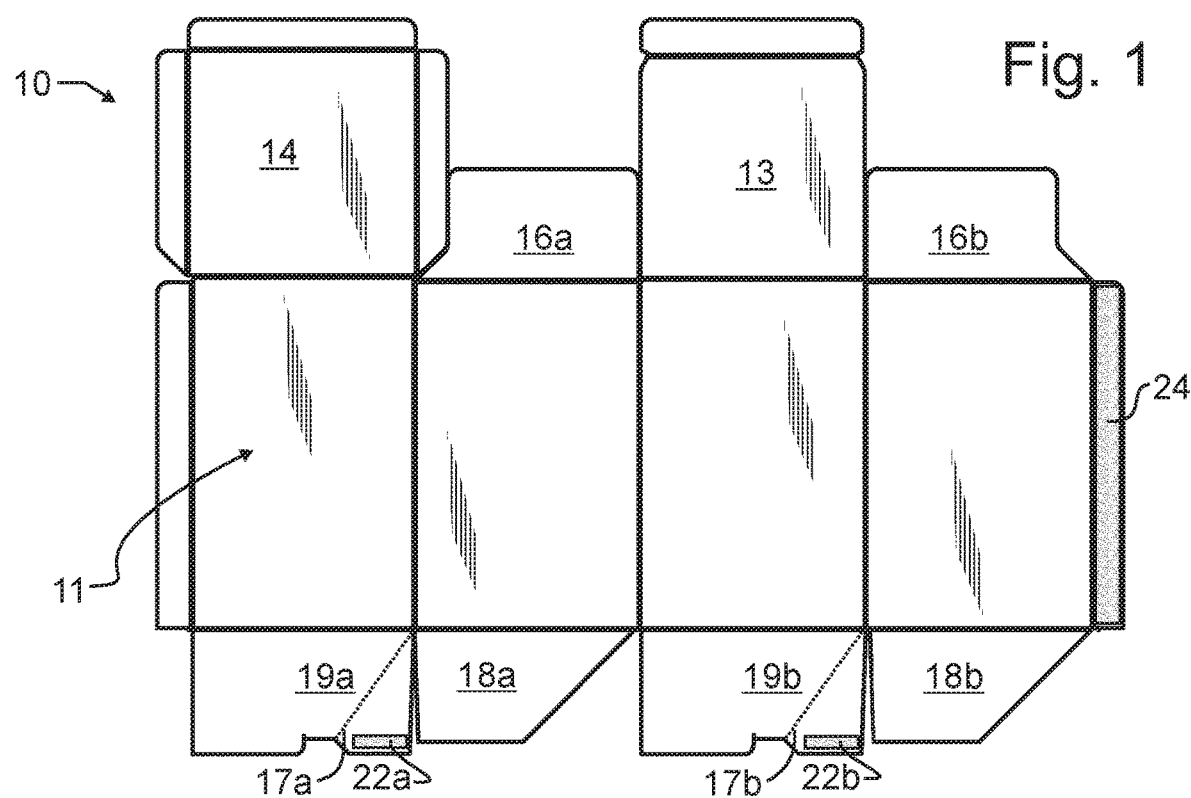
FIG. 1 illustrates a preferred embodiment take-back box blank designed in accord with the teachings of the present invention from an inside plan view.
Figure 2:
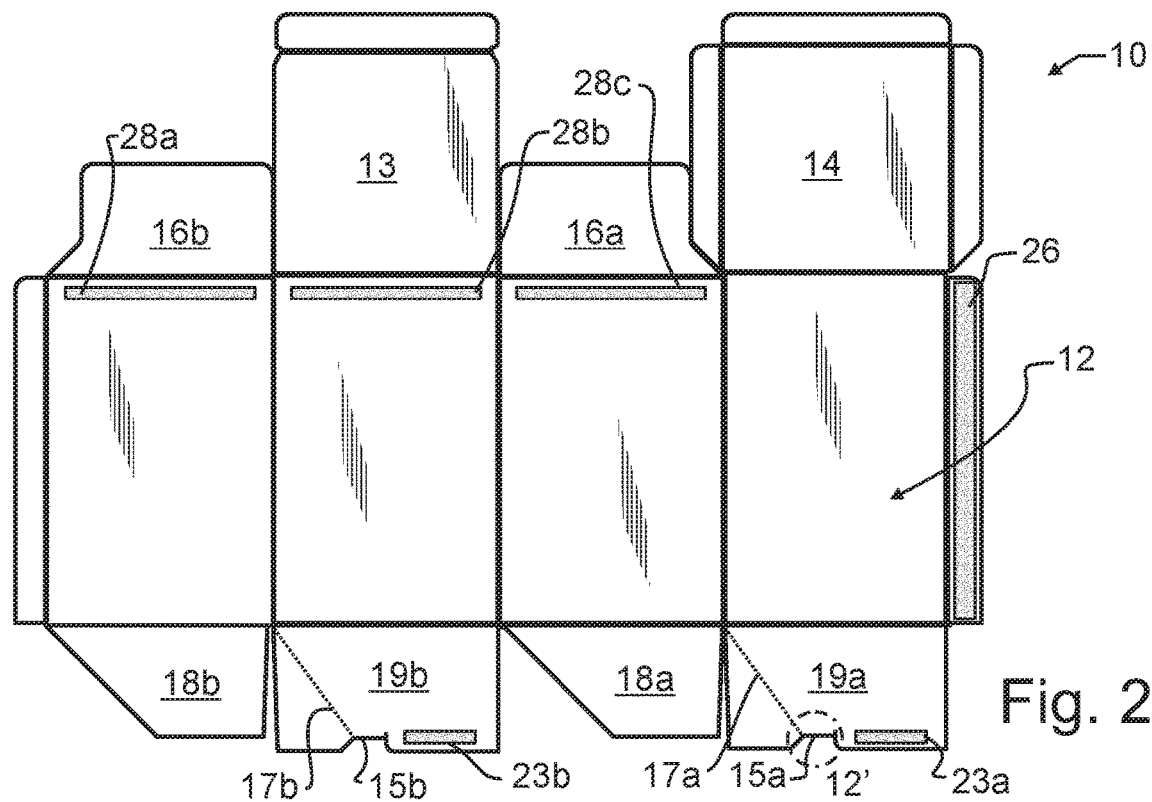
FIG. 2 illustrates the preferred embodiment take-back box blank of FIG. 1 from an outside plan view.
Figure 3:
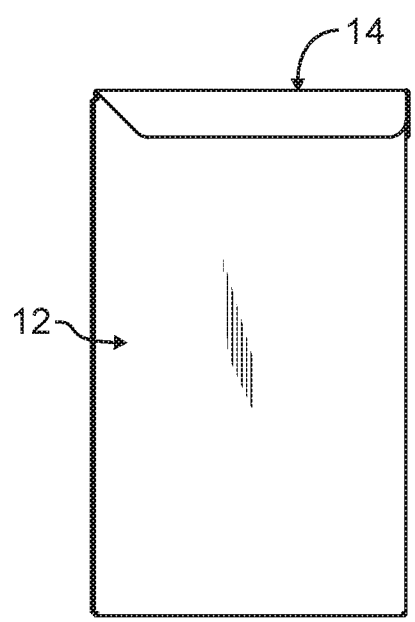
FIGS. 3-7 illustrate the preferred embodiment take-back box assembled from the blank of FIGS. 1 and 2 from a left side elevational view, a top view, a projected view, a front view, and a rear elevational view, respectively.
Figure 4:
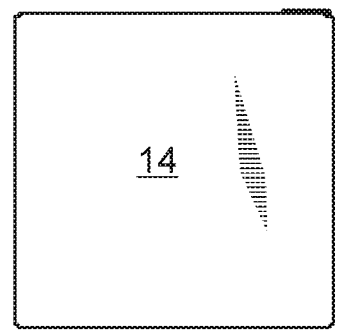
Figure 5:
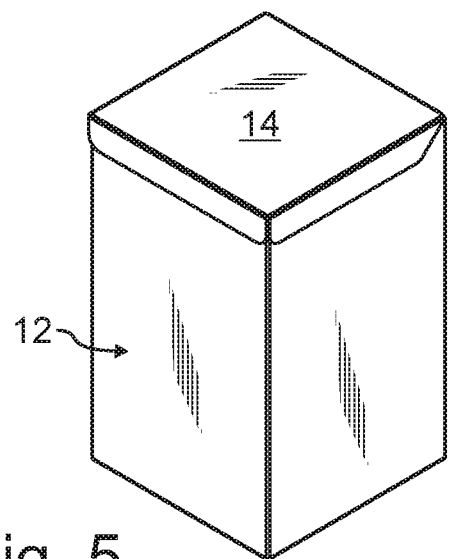

FIGS. 1 and 2 illustrate a preferred embodiment take-back box blank, showing the eventual box inside 11 and box outside 12 surfaces, respectively. As evident from these Figures, it is apparent that the box blank may be stamped or otherwise cut from a larger single sheet in a single operation. Box 10 is preferably provided with an inside top lid 13, a pair of top lid side flaps 16*a, b*, and an outside top lid 14. Defining the bottom of box 10 are a pair of bottom side flaps 18*a, b*, and a pair of bottom main flaps 19*a, b*. Within each one of the pair of bottom main flaps 19*a, b* there is provided a single bottom main flap crease line, identified as 17*a* and 17*b* in the Figures. There is also a single notch 15*a, b* provided within each one of the pair of bottom main flaps 19*a, b*.

When the box blank as illustrated in FIGS. 1 and 2 has been die cut or otherwise formed, at each of the illustrated solid line junctions a fold line will preferably be formed, as will the bottom main flap crease lines, identified as 17*a* and 17*b*. When box 10 is fabricated from a preferred material such as corrugated cardboard, the techniques for cutting the box blank and forming appropriate creases in the blank are well known and understood by those skilled in the box-making art.

Once the box blank is cut and fold lines and creases formed, a suitable tape, applied adhesive, or other equivalent fastener will be applied at several key areas. In a preferred embodiment, these are tapes, each formed using a double-sided adhesive. To facilitate visual identification and manipulation, in a most preferred embodiment a black polyethylene foam having a pressure sensitive adhesive on both surfaces is used, and a white waxed or similarly coated release paper of slightly greater width than the foam adhesive tape covers the major surface opposite the box blank. On the box blank inside surface 11 visible in FIG. 1, a pair of bottom tapes 22*a, b* are applied to bottom main flaps 19*a, b*, respectively. Three additional top tapes 28*a-c* are applied, one to each of the three side surfaces in positions that will align on the assembled box with the exposed flaps of outside top lid 14. Finally, a side glue 24 is applied along the rightmost flap in FIG. 1.

While not essential to the present invention, the top tapes 28*a-c* are most preferably aligned in a longitudinal direction coaxially with each other. This allows a single dispenser to apply the tape, with single direction or axis of relative movement between the box and dispenser. For exemplary and non-limiting purpose, the box may be traveling in a single direction along a conveyor, while a stationary applicator intermittently applies and cuts the tape.

In addition, the top tapes 28 and bottom tapes 22*a, b* are preferably aligned in a longitudinal direction parallel with each other. This parallel alignment also simplifies the application process during manufacture, allowing several tape dispensers to apply tape to the box simultaneously.

Next, box blank 10 is flipped, exposing box outside 12. Bottom tapes 23*a, b* may then be applied to bottom main flaps 19*a, b*, respectively. Finally, a side glue 26 is applied along the rightmost flap in FIG. 2. Once again, while a glue is discussed and preferred for side glue 26, it will be understood that any suitable adhesive or fastener may be applied or incorporated.

The order of application is not critical to the present invention, and so either the inner tapes and glues may be applied to box inside 11 first, or the sequence may be reversed and the outer tapes and glues may be applied to box outside 12 first. Similarly, either the tapes or glues may be applied first, depending upon the requirements of the equipment used for application of each.

Figure 6:
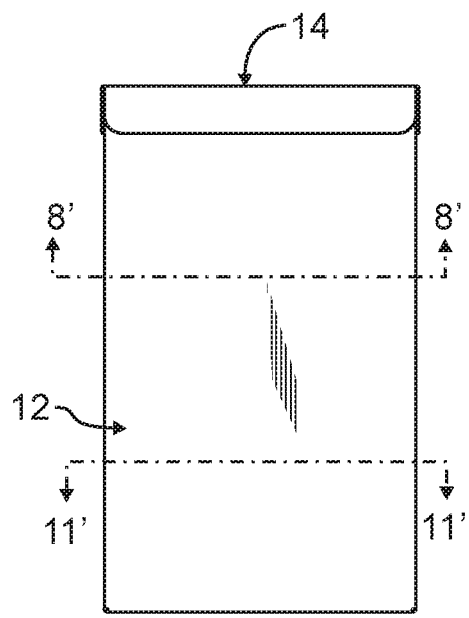
Figure 7:
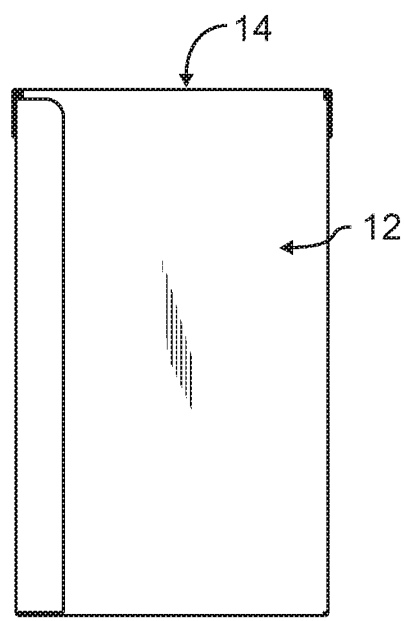
Figure 9:
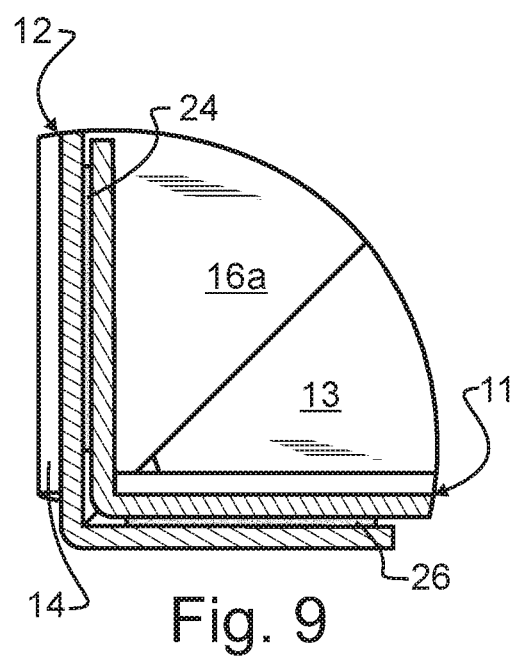
FIG. 9 illustrates the preferred embodiment take-back box of FIG. 8 from a further partial and enlarged section view taken along section line 9' of FIG. 8 detailing the side wall closure construction.

At this point, initial assembly of the blank into a box involves the formation of a rectangular cross-section such as taken along section lines 8' and 11' of FIG. 6. This is accomplished by folding the blank along each of the vertical fold lines in FIGS. 1 and 2 to form four vertical side walls, and then affixing each of side glue 24 and side glue 26 to an adjacent vertical side wall as best illustrated in FIG. 9.

At the same time or subsequent thereto, bottom side flaps 18*a, b* are folded into the interior space created thereby. Next, the waxed release paper is removed from bottom tapes 22*a, b*. Finally, bottom main flaps 19*a, b* are each individually pressed against the adjacent one of bottom side flaps 18*a, b*, thereby forming a bond through bottom tapes 22*a, b*. At this stage in the assembly, only bottom tapes 22*a, b* and each of side glue 24 and side glue 26 are affixed. Bottom tapes 23*a, b* and top tapes 28 are each still covered by waxed release paper.

Because of the provision of bottom main flap crease lines 17*a, b*, the vertical fold line separating bottom side flap 18*a* from bottom main flap 19*b* may be bent to reduce the angle therebetween to a nearly zero degree angle, bringing bottom side flap 18*a* into substantially a parallel plane immediately adjacent to bottom main flap 19*b*. At the same time, bottom side flap 18*b* will come into substantially a parallel plane immediately adjacent to bottom main flap 19*a*. This arrangement defines a first configuration for box 10, which is the original kit configuration. As may be appreciated, this first kit configuration is a double-thick flat configuration. Consequently, box 10 may be inserted together with a liner 40 into a secondary shipping carton, and may conveniently be delivered to a kiosk such as those identified herein above or to other location where the present invention may then be reconfigured and further assembled. In this first original kit configuration, substantial inventory of boxes 10 with associated liners 40 may be stored with very few voids and wasted space. This reduces shipping cost, provides a more durable package during shipping thereby reducing in-transit loss and delay, and reduces inventory space and expense. In addition, the secondary shipping carton excludes dust or other contamination from coating either box 10 or liner 40, thereby preserving the vital adhesive surfaces during storage until actually needed for use within a kiosk and during transport.

Figure 8:
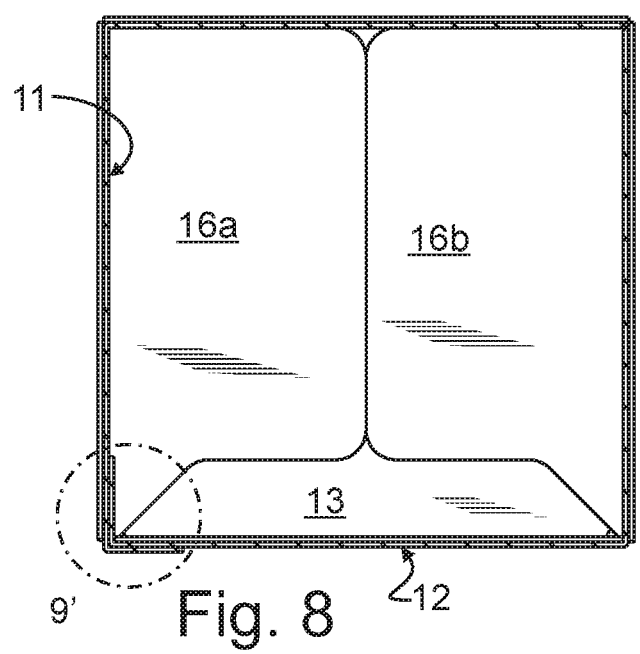
FIG. 8 illustrates the preferred embodiment take-back box of FIGS. 3-7 from a sectional view taken along section line 8' of FIG. 6 looking toward the top of the box.
Figure 13:
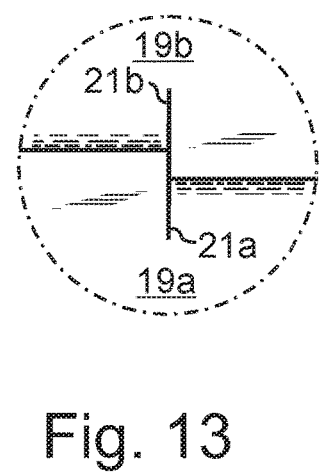
FIG. 13 illustrates the assembled preferred embodiment take-back box of FIG. 10 from a partial and enlarged view taken along section line 13' detailing engaged notches 21a, 21b.

When delivered to a kiosk or the like, a person such as someone charged with the responsibility of maintaining the kiosk will convert box 10 and liner 40 from this first original kit configuration to a second receptacle configuration. The sequence for this is to gently pull the bottom of the box apart in the middle, reshaping box 10 toward but not to the rectangular cross-section of FIGS. 8 and 11, thereby exposing the bottom tapes 23*a, b*. The waxed release paper is removed, and the box is then pulled farther apart, again farther toward but not to the rectangular cross-section of FIGS. 8 and 11. When mechanically advantageous, the person will then push in the furthest two vertical edges of the box to make the bottom rectangular. When this is done, the two notches 15*a* and 15*b* will slide against each other, and eventually as box 10 takes the rectangular cross-section, slits 21*a, b* will align with each other, allowing the two slits to couple or press into each other, as best visible in FIG. 10 and the enlarged view of FIG. 13. With the box upright, the person will then press the bottom of the box flat to engage the bottom tapes 23*a, b* with bottom side flaps 18*b, a*, respectively. This engagement retains box 10 in the rectangular cross-section illustrated in FIGS. 8 and 11.

Figure 12:
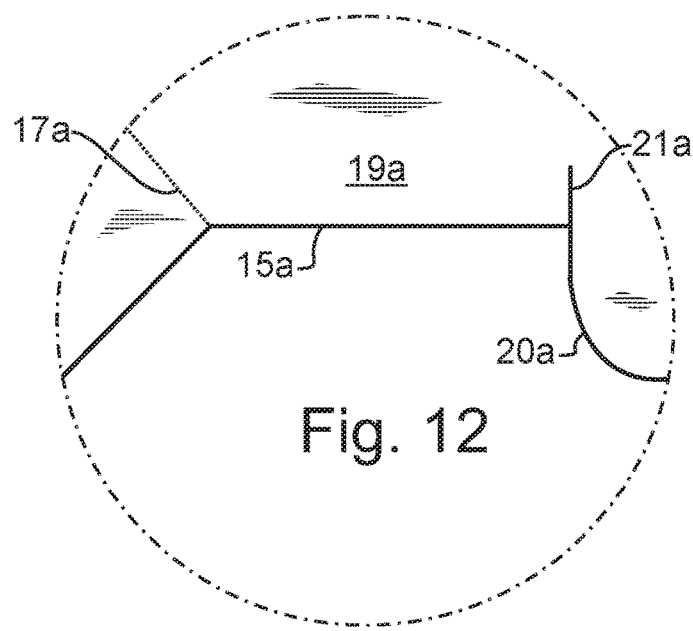
FIG. 12 illustrates the preferred embodiment take-back box blank of FIG. 2 from a partial and enlarged view taken along section line 12' detailing the notch and slit geometry of the bottom main flaps.

From the illustration of FIG. 12, notch 15a comprises a portion of a box edge. The edge of the box defines lines meeting adjacent to bottom main flap crease line 17a, b at an obtuse angle to each other. The angle of intersection is not essential to the present invention, and so will be selected by a designer after review and consideration of the present disclosure. Likewise, the ultimate indentation defined by notch 15a is not critical and will be varied by a reasonably skilled designer. Notch 15b will in most embodiments have like or similar geometry.

Figure 10:
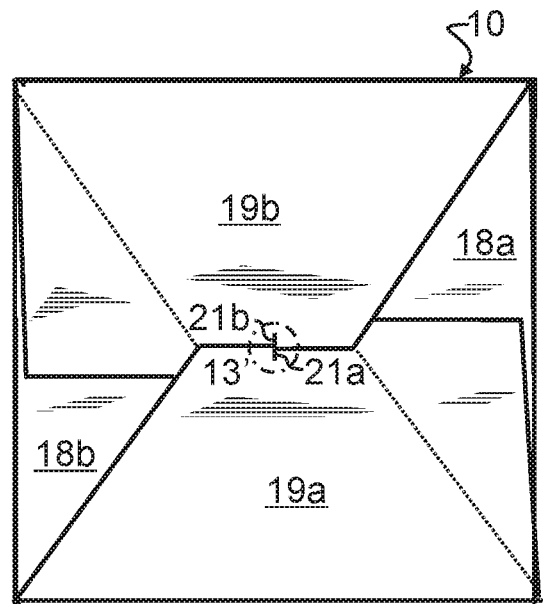
FIG. 10 illustrates the preferred embodiment take-back box of FIGS. 3-7 from a bottom view.
Figure 11:
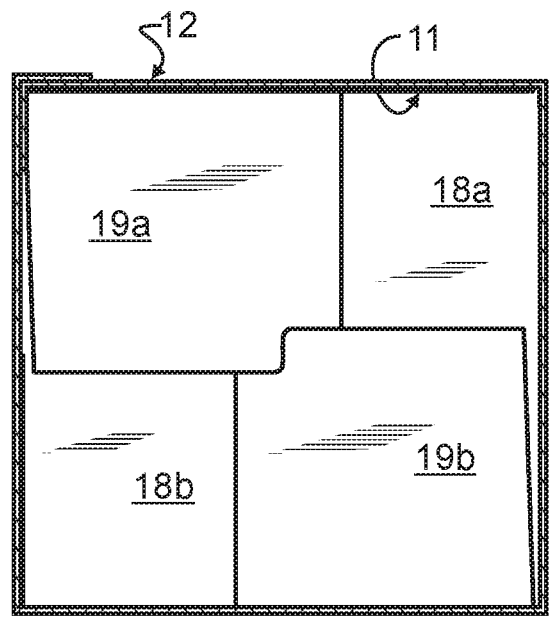
FIG. 11 illustrates the preferred embodiment take-back box of FIGS. 3-7 from a sectional view taken along section line 11' of FIG. 6 looking toward the bottom of the box.

These notches 15a, b allow the box edges along bottom main flaps 19a, b to gradually slide together, and then slide along the parallel edges at the full depth of notches 15a, 15b. Finally, the box edges eventually slide sufficiently to align notches 15a, b with each other, and the bottom main flaps 19a, b slide together into overlapping relationship such as visible in FIG. 10, held against further relative movement by the engagement of slit 21a with slit 21b such as visible in FIG. 13. In the preferred embodiment, a pair of curved notch entry edges 20a, b define the rightmost portion of the notch, as also clearly illustrated in FIG. 12. Again, once slits 21a, b align and engage with each other as visible in FIG. 13, the person will engage the bottom tapes 23a, b with bottom side flaps 18b, a, respectively, to permanently hold the box bottom in this rectangular geometry such as illustrated in FIGS. 10 and 11.

Next, the person will install liner bag 40 over the top edges of the vertical sidewalls of box 10. In this process, each of the inside top lid 13, outside top lid 14, and top lid side flaps 16a, b will be flexed along the horizontal fold lines into a position more nearly parallel to each of the most adjacent vertical side walls than perpendicular thereto. Since liner bag 40 wraps about and thereby snugs the flaps, the combined box 10 and liner bag 40 is of very predictable and stable dimension, and may therefore be designed to fit snugly within a kiosk. Consequently, the wrapping of liner bag 40 about the flaps of box 10 makes it much less likely that an errant medication bottle will be dropped outside of the liner bag. Furthermore, this arrangement helps to reduce the chance of user error during installation, both in proper placement of the combined box and bag within the kiosk and in the proper positioning of the box flaps that could otherwise interfere.

Since for most applications there is a possibility that liquids may be deposited into the thus formed receptacle defined by the open topped box 10 and liner bag 40, in the preferred embodiment an absorbent pouch is provided within the first kit configuration. In such case, this absorbent pouch is inserted into liner bag 40. The process of converting box 10 and liner 40 from the first original kit configuration to a second receptacle configuration is now complete. Box 10 and liner 40 in this second receptacle configuration will now be inserted into a kiosk or other apparatus, and will receive and retain pharmaceuticals and other medications therein.

Polyethylene, including modifications thereof such as High-Density PolyEthylene (HDPE) or Ultra-High Molecular Weight polyethylene (UHMW), is readily available and has outstanding resistance to solvents of nearly all types. Since polyethylene is also readily combustible, enough so that it is a common and significant component of many commercial candle compositions, liner 40 may also readily be fabricated from this well-known and commonly used combustible material. While polyethylene is preferred, owing to the ready availability, clean and ready combustibility, and also outstanding resistance to solvents of nearly all types, other plastic compositions are known that may be substituted therefore.

When the box 10 and liner 40 in the second receptacle configuration is to be replaced, such as when full or otherwise scheduled or determined, box 10 and bag liner 40 are reconfigured to a third transport configuration that is configured to transport the contents of bag liner 40 to a disposal or other facility. This reconfiguration from the second receptacle configuration to third transport configuration also involves only a few intuitive steps.

Figure 14:
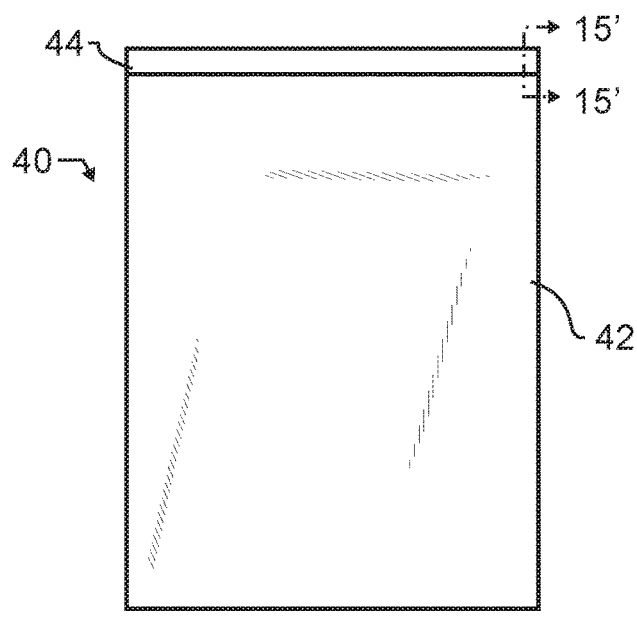
FIG. 14 illustrates a preferred embodiment take-back liner designed in accord with the teachings of the present invention from a side elevational view.
Figure 15:
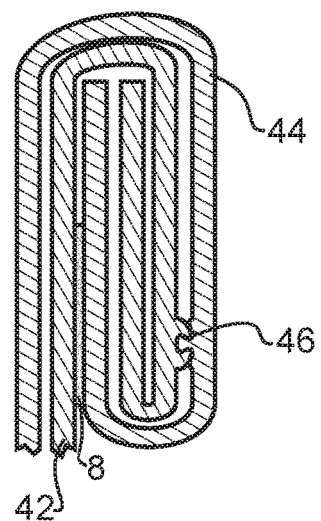
FIG. 15 illustrates the preferred embodiment take-back liner of FIG. 14 from a sectional view taken along section line 15' of FIG. 14.

A person will unfold bag liner 40 from the box 10. Air may be squeezed out by draping liner 40 over an edge of box 10. Then liner zip 46 will be closed. For exemplary and non-limiting purpose, a rib and groove closure is illustrated in FIG. 14 as the liner zip 46. This type of closure is convenient to use and well understood by most people, which helps to reduce user error and thereby provide better consistency and conformity for compliant and secure transportation. Nevertheless, other known types of bag closures will be understood to be incorporated herein as well, including but not limited to the various types of closures illustrated in the patents incorporated by reference herein above.

Next the person will remove release paper from liner tape 48 located on liner side wall 42 of liner bag 40. The top of liner 40 is folded over the liner zip 46 twice, so that liner side wall 42 is adhered to liner side wall 44 by liner tape 48. This removes strain from liner zip 46, helping to ensuring liner zip 46 stays closed. Furthermore, the dual fold and adhesive provides evidence of tampering, should such tampering occur after closure if liner 40.

Box 10 will next need closed and sealed. Top lid side flaps 16a, b are first closed. Next, inside top lid 13 is closed with one tab insert as visible in FIGS. 8 and 9. The waxy release paper is now removed from the three tapes 28a-c. The outside top lid 14 of box 10 is then closed and sealed by first pushing the single flap on the front against the front vertical side wall and thereby activating the exposed adhesive, and subsequently pressing the side flaps down as well to activate the exposed adhesive. When sealed in this manner, the top lid becomes a tamper resistant barrier preventing the box from being reopened without significant destruction to the box, clearly identifying any intrusion or tampering. Box 10 and liner 40 are now in the third transport configuration, ready for shipment.

While the various adhesive strips are illustrated as being affixed to one surface as illustrated in FIGS. 1 and 2, it will be apparent and understood that they may instead be affixed to the surface that will be opposed thereto when the adhesive is active.

Where hazardous materials or highly-controlled medications are received within box 10 and liner 40, the closure of box 10 as illustrated in FIGS. 3-7 and the closure of liner 40 as illustrated in FIG. 14 provides a set of secure seals that will show when tampered with. This allows monitoring and verification of safe and secure transport. In further alternative embodiments, where desired and appropriate one or both of box 10 and liner 40 may be serialized for further tracking and record keeping. Other types of tamper evident seals such as but not limited to those incorporated by reference herein above may also or alternatively be used in various embodiments of the invention.

While user error may be presumed to be independent of the design of the "bag-in-a-box," this is not true. Some user errors simply cannot be anticipated, but other errors can be. The present invention addresses several of these very effectively.

As may be now better appreciated, box 10 requires no separate packing tape for assembly, and the location and size of fasteners is predetermined. Consequently, the strength and positioning of the adhesive securement is very predictable and repeatable.

The box design in combination with the pre-affixed tapes 28 and 22a, b also simplifies reconfiguration of the box from the first kit configuration through to the third transport configuration. As a result, a person reconfiguring the box has far less opportunity for error than in the prior art. This provides better consistency in assembly and reconfiguration, further ensuring compliant and secure contents throughout the process.

These are not the only advantage of pre-affixed tapes 28 and 22a, b. Secure transport of hazardous and highly regulated medications not only requires tamper evident seals and proper closure, but also a package that is sufficiently durable to survive transit. As already noted herein above, a failure of the box either at the time of installation in a kiosk or during transport can result in the need for a hazmat team to be mobilized. As a baseline, the strength requirement is set by DOT Packing Group II specifications which includes a corner drop test at rated weight from a four foot elevation.

The provision of pre-affixed tapes, engaging slits 21a, b, and reinforced edges all provide exceptional synergy to yield an exceptionally strong box 10. The double vertical side joint as illustrated in FIG. 9 provides sufficient reinforcement to meet this requirement. Similarly, the multi-layer top and bottom closures likewise provide extra structural strength. The bottom strength is further enhanced by slits 21a, b. All box edges are either double-layered, such as on both sides of the vertical sidewall seam formed by glue 24, 26 and around the perimeter of outside top lid 14 defined by the flaps folding onto the side walls, but also along each and every vertical sidewall edge which is reinforced by an adjacent panel at a ninety degree angle thereto. This perpendicular reinforcement substantially stiffens each and every edge. Even bottom main flap crease lines 17a, b are most preferably creases, rather than alternative perforations usually used to form similar flexures. The preferred embodiment meets and exceeds the specifications, while as noted providing a transportation apparatus that is intuitive to use and less prone to user error. By providing an improved take back box, liner, and kit, the present invention helps to get prescriptions properly disposed more conveniently and for less total cost than heretofore possible.

While the foregoing details what is felt to be the preferred embodiment of the invention, no material limitations to the scope of the claimed invention are intended. Further, features and design alternatives that would be obvious to one of ordinary skill in the art are considered to be incorporated herein. The scope of the invention is set forth and particularly described in the claims herein below.

We claim:

1. In combination, a box and a bag liner retained within the box, said combination box and bag liner having a first substantially void free flat receptacle configuration for storage and shipping of box and liner kits, a second receptacle configuration into which articles may be inserted, and a third transport configuration enclosing said articles within each of said box and said bag liner,
    said box comprising:
        a box blank fabricated from a unitary planar sheet, said box blank having a plurality of fold lines defining first, second, third, and fourth vertical side walls hinged to adjacent ones of said side walls,
        first and second bottom side flaps hinged to first and third vertical side walls, respectively,
        a first bottom main flap hinged to said second vertical side wall, having
            at least one crease line formed therein dividing said first bottom main flap into first and second portions, and
            at least one notch intersecting with said at least one crease line and terminating with a slit, said slit formed in said second portion of said first bottom main flap,
        a second bottom main flap hinged to said fourth vertical side wall, having
            at least one crease line formed therein dividing said second bottom main flap into first and second portions, and
            at least one notch intersecting with said at least one crease line and terminating with a slit, said slit formed in said second portion of said second bottom main flap,
        an inside top lid hinged to a one of said first, second, third, and fourth vertical side walls,
        an outside top lid hinged to a first one of said first, second, third, and fourth vertical side walls, and first, second and third outside top lid side flaps each hinged to said outside top lid;
    a first tape strip affixing said first bottom side flap to said first bottom main flap on a first side of said first bottom main flap crease line;
    a second tape strip affixing said second bottom side flap to said second bottom main flap on a first side of said second bottom main flap crease line;
    a third tape strip affixed to a one of said second bottom side flap and said first bottom main flap and disconnected from another of said second bottom side flap and said first bottom main flap when said combination box and bag liner is in said first substantially void free flat receptacle configuration, said third tape strip further configured to affix said second bottom side flap to said first bottom main flap on a second side of said first bottom main flap crease line when said combination box and bag liner is in said second receptacle configuration into which articles may be inserted and configured to affix said second bottom side flap to said first bottom main flap on a second side of said first bottom main flap crease line when said combination box and bag liner is in said third transport configuration;
    a fourth tape strip affixed to a one of said first bottom side flap and said second bottom main flap and disconnected from another of said first bottom side flap and said second bottom main flap when said combination box and bag liner is in said first substantially void free flat receptacle configuration, said fourth tape strip further configured to affix said first bottom side flap to said second bottom main flap on a second side of said second bottom main flap crease line when said combination box and bag liner is in said second receptacle configuration into which articles may be inserted and configured to affix said second bottom side flap to said first bottom main flap on a second side of said first bottom main flap crease line when said combination box and bag liner is in said third transport configuration;
    said first bottom main flap slit disconnected from said second bottom main flap slit when said combination box and bag liner is in said first substantially void free flat receptacle configuration and coupled with said second bottom main flap slit when said combination box and bag liner is in said second receptacle configuration and when said combination box and bag liner is in said third transport configuration;

a fifth tape strip affixed to a one of said first, second, third, and fourth vertical side walls and said outside top lid and disconnected from each other of said first, second, third, and fourth vertical side walls and said outside top lid when said combination box and bag liner is in said first substantially void free flat receptacle configuration and when said combination box and bag liner is in said second receptacle configuration, said fifth tape strip configured to affix a second one of said first, second, third, and fourth vertical side walls to said outside top lid when said combination box and bag liner is in said third transport configuration;

a sixth tape strip affixed to a one of said first, second, third, and fourth vertical side walls and said outside top lid and disconnected from each other of said first, second, third, and fourth vertical side walls and said outside top lid when said combination box and bag liner is in said first substantially void free flat receptacle configuration and when said combination box and bag liner is in said second receptacle configuration, said sixth tape strip configured to affix a third one of said first, second, third, and fourth vertical side walls to said outside top lid when said combination box and bag liner is in said third transport configuration;

a seventh tape strip affixed to a one of said first, second, third, and fourth vertical side walls and said outside top lid and disconnected from each other of said first, second, third, and fourth vertical side walls and said outside top lid when said combination box and bag liner is in said first substantially void free flat receptacle configuration and when said combination box and bag liner is in said second receptacle configuration, said seventh tape strip configured to affix a fourth one of said first, second, third, and fourth vertical side walls to said outside top lid when said combination box and bag liner is in said third transport configuration;

said bag liner comprising:
  a pair of opposed side walls affixed to each other to define a bag having an open top;
  a liner zip configured to close said open top when said combination box and bag liner is in said third transport configuration; and
  a liner tape displaced farther from said open top than said liner zip, and configured to secure a twice-folded closed top of said bag against a one of said pair of opposed side walls when said combination box and bag liner is in said third transport configuration.

2. The combination box and bag liner retained within the box of claim 1, wherein said planar blank further comprises a first vertical flap hinged to said first vertical side wall and a second vertical flap hinged to said fourth vertical side wall, said first vertical flap affixed to said fourth vertical side wall and said second vertical flap affixed to said first vertical side wall.

3. The combination box and bag liner retained within the box of claim 2, wherein each one of said first, second, third, and fourth vertical side walls are defined by a generally planar surface and four edges, and each one of said four edges is joined to another box blank member extending therefrom in a perpendicular plane when said combination box and bag liner is in said first substantially void free flat receptacle configuration and when said combination box and bag liner is in said second receptacle configuration and when said combination box and bag liner is in said third transport configuration.

4. The combination box and bag liner retained within the box of claim 1, wherein said box blank comprises corrugated cardboard.

5. The combination box and bag liner retained within the box of claim 1, wherein said bag liner comprises polyethylene.

6. A box having a first substantially void free flat receptacle configuration, a second receptacle configuration into which articles may be inserted, and a third transport configuration enclosing said articles within said box, comprising:

a box blank fabricated from a unitary planar sheet, said box blank having a plurality of fold lines defining
  first, second, third, and fourth vertical side walls hinged to adjacent ones of said side walls,
  first and second bottom side flaps hinged to first and third vertical side walls, respectively,
  a first bottom main flap hinged to said second vertical side wall, having
    at least one crease line formed therein dividing said first bottom main flap into first and second portions, and
    at least one notch intersecting with said at least one crease line and terminating with a slit, said slit formed in said second portion of said first bottom main flap,
  a second bottom main flap hinged to said fourth vertical side wall, having
    at least one crease line formed therein dividing said second bottom main flap into first and second portions, and
    at least one notch intersecting with said at least one crease line and terminating with a slit, said slit formed in said second portion of said second bottom main flap,
  an inside top lid hinged to a one of said first, second, third, and fourth vertical side walls,
  an outside top lid hinged to a first one of said first, second, third, and fourth vertical side walls, and
  first, second and third outside top lid side flaps each hinged to said outside top lid;

a first tape strip affixing said first bottom side flap to said first bottom main flap on a first side of said first bottom main flap crease line;

a second tape strip affixing said second bottom side flap to said second bottom main flap on a first side of said second bottom main flap crease line;

a third tape strip affixed to a one of said second bottom side flap and said first bottom main flap and disconnected from another of said second bottom side flap and said first bottom main flap when said box is in said first substantially void free flat receptacle configuration, said third tape strip further configured to affix said second bottom side flap to said first bottom main flap on a second side of said first bottom main flap crease line when said box is in said second receptacle configuration into which articles may be inserted and configured to affix said second bottom side flap to said first bottom main flap on a second side of said first bottom main flap crease line when said box is in said third transport configuration;

a fourth tape strip affixed to a one of said first bottom side flap and said second bottom main flap and disconnected from another of said first bottom side flap and said second bottom main flap when said box is in said first substantially void free flat receptacle configuration, said fourth tape strip further configured to affix said first bottom side flap to said second bottom main flap on a second side of said second bottom main flap crease line when said box is in said second receptacle configuration into which articles may be inserted and configured to affix said second bottom side flap to said first bottom main flap on a second side of said first bottom main flap crease line when said box is in said third transport configuration;

said first bottom main flap slit disconnected from said second bottom main flap slit when said box is in said first substantially void free flat receptacle configuration and coupled with said second bottom main flap slit when said box is in said second receptacle configuration and when said box is in said third transport configuration;

a fifth tape strip affixed to a one of said first, second, third, and fourth vertical side walls and said outside top lid and disconnected from each other of said first, second, third, and fourth vertical side walls and said outside top lid when said box is in said first substantially void free flat receptacle configuration and when said box is in said second receptacle configuration, said fifth tape strip configured to affix a second one of said first, second, third, and fourth vertical side walls to said outside top lid when said box is in said third transport configuration;

a sixth tape strip affixed to a one of said first, second, third, and fourth vertical side walls and said outside top lid and disconnected from each other of said first, second, third, and fourth vertical side walls and said outside top lid when said box is in said first substantially void free flat receptacle configuration and when said box is in said second receptacle configuration, said sixth tape strip configured to affix a third one of said first, second, third, and fourth vertical side walls to said outside top lid when said box is in said third transport configuration;

a seventh tape strip affixed to a one of said first, second, third, and fourth vertical side walls and said outside top lid and disconnected from each other of said first, second, third, and fourth vertical side walls and said outside top lid when said box is in said first substantially void free flat receptacle configuration and when said box is in said second receptacle configuration, said seventh tape strip configured to affix a fourth one of said first, second, third, and fourth vertical side walls to said outside top lid when said box is in said third transport configuration.

7. The box of claim 6, wherein said planar blank further comprises a first vertical flap hinged to said first vertical side wall and a second vertical flap hinged to said fourth vertical side wall, said first vertical flap affixed to said fourth vertical side wall and said second vertical flap affixed to said first vertical side wall.

8. The box of claim 7, wherein each one of said first, second, third, and fourth vertical side walls are defined by a generally planar surface and four edges, and each one of said four edges is joined to another box blank member extending therefrom in a perpendicular plane when said combination box and bag liner is in said first substantially void free flat receptacle configuration and when said combination box and bag liner is in said second receptacle configuration and when said combination box and bag liner is in said third transport configuration.

9. The box of claim 6, wherein said box blank comprises corrugated cardboard.

\* \* \* \* \*